US010441160B2

(12) United States Patent
Coleman

(10) Patent No.: US 10,441,160 B2
(45) Date of Patent: *Oct. 15, 2019

(54) METHOD AND SYSTEM FOR CLASSIFYING OPTIC NERVE HEAD

(71) Applicant: DELPHINIUM CLINIC LTD., Co. Dublin (IE)

(72) Inventor: Kate Coleman, Co. Dublin (IE)

(73) Assignee: DELPHINIUM CLINIC LTD., Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/115,242

(22) Filed: Aug. 28, 2018

(65) Prior Publication Data

US 2018/0360305 A1 Dec. 20, 2018

Related U.S. Application Data

(63) Continuation of application No. 15/821,626, filed on Nov. 22, 2017.

(30) Foreign Application Priority Data

Nov. 22, 2016 (IE) .................................. S2016/0260

(51) Int. Cl.
*A61B 3/00* (2006.01)
*A61B 3/14* (2006.01)
(Continued)

(52) U.S. Cl.
CPC .............. *A61B 3/0025* (2013.01); *A61B 3/12* (2013.01); *A61B 3/1233* (2013.01); *A61B 3/14* (2013.01);
(Continued)

(58) Field of Classification Search
CPC ....... A61B 3/0025; A61B 3/12; A61B 3/1233; A61B 3/14; G06T 7/10; G06T 7/0014; G06T 2207/10101; G06T 2207/20081; G06T 2207/20084; G06T 2207/30041; G06T 2207/30101; G06K 9/0061; G06K 9/00617

See application file for complete search history.

(56) References Cited

U.S. PATENT DOCUMENTS 7,992,999 B2 8/2011 Xu et al.
8,705,826 B2 4/2014 Liu et al.
(Continued)

FOREIGN PATENT DOCUMENTS

WO 2011059409 A1 5/2011

OTHER PUBLICATIONS

Jonas JB, Fernández MC. Shape of the neuroretinal rim and position of the central retinal vessels in glaucoma. British Journal of Ophthalmology 1994;78:99-102, ISSN: 0007-1161.
(Continued)

*Primary Examiner* — Brenda C Bernardi
(74) *Attorney, Agent, or Firm* — Adler Pollock & Sheehan P.C

(57) ABSTRACT

Provided are a method and system for identifying and classifying the owner, age and health of an optic nerve head and its vasculature based on analysis of vector relationships of blood vessels and the neuroretinal rim within an image of the optic nerve head to each other.

15 Claims, 11 Drawing Sheets

(51) Int. Cl.
*A61B 3/12* (2006.01)
*G06T 7/00* (2017.01)
*G06T 7/10* (2017.01)
*G06K 9/00* (2006.01)

(52) U.S. Cl.
CPC ....... *G06K 9/0061* (2013.01); *G06K 9/00617* (2013.01); *G06T 7/0014* (2013.01); *G06T 7/10* (2017.01); *G06T 2207/10101* (2013.01); *G06T 2207/20081* (2013.01); *G06T 2207/20084* (2013.01); *G06T 2207/30041* (2013.01); *G06T 2207/30101* (2013.01)

(56) References Cited

U.S. PATENT DOCUMENTS

| | | | |
|---|---|---|---|
| 9,008,391 | B1 | 4/2015 | Solanki et al. |
| 2004/0114109 | A1* | 6/2004 | Soliz ............... A61B 3/12 351/221 |
| 2005/0200808 | A1* | 9/2005 | Wyatt .............. A61B 3/112 351/246 |
| 2006/0098867 | A1* | 5/2006 | Gallagher ......... G06K 9/0061 382/167 |
| 2010/0007726 | A1* | 1/2010 | Barbieri .......... G06K 9/00221 348/78 |
| 2010/0277691 | A1 | 11/2010 | Huang et al. |
| 2011/0091083 | A1* | 4/2011 | Liu .................. A61B 3/12 382/128 |
| 2012/0157820 | A1 | 6/2012 | Zhang et al. |
| 2012/0213423 | A1 | 8/2012 | Xu et al. |
| 2012/0230564 | A1* | 9/2012 | Liu .................. A61B 3/12 382/128 |
| 2012/0274898 | A1 | 11/2012 | Sadda et al. |
| 2012/0287401 | A1* | 11/2012 | Bizios ............. A61B 3/0025 351/206 |
| 2014/0276025 | A1* | 9/2014 | Durbin ............. A61B 5/4842 600/427 |
| 2016/0345819 | A1* | 12/2016 | Jayasundera ...... A61B 3/0025 |
| 2018/0096226 | A1* | 4/2018 | Aliabadi .......... G06K 9/6219 |
| 2018/0137335 | A1* | 5/2018 | Kim ................. G06K 9/00604 |

OTHER PUBLICATIONS

PCT/EP2017/080116 International Search Report dated Jan. 31, 2018.
PCT/EP2017/080116 Written Opinion of the International Searching Authority dated Jan. 31, 2018.
Claro et al., "Automatic Glaucoma Detection Based on Optic Disc Segmentation and Texture Feature Extraction", CLEI Electronic Journal, vol. 19, No. 2, Paper 4, Aug. 2016, 10 pages.
Drozd et al., "An Algorithm for Retina Features Extraction Based on Position of the Blood Vessel Bifurcation", CCBR 2012: Biometric Recognition, pp. 308-315.
Extended European Search Report received in European Patent Application No. 18187334.0 dated Dec. 3, 2018, 5 pages.
Gulshan et al., "Development and Validation of a Deep Learning Algorithm for Detection of Diabetic Retinopathy in Retinal Fundus Photographs", JAMA, AMA, Nov. 29, 2016, pp. E1-E9.
Haleem et al., "Regional Image Features Model for Automatic Classification between Normal and Glaucoma in Fundus and Scanning Laser Ophthalmoscopy (SLO) Images", Springer, J. Med. Syst., vol. 40, No. 132, 19 pages.
Muhammad et al., "Hybrid Deep Learning on Single Wide-Field Optical Coherence Tomography Scans Accurately Classifies Glaucoma Suspects", J. Glaucoma., vol. 26, No. 12, Dec. 2017, 21 pages.

* cited by examiner

For each sub-image of CD, extract circles at radio 50,55,60,65,70,80,90 pixels

METHOD AND SYSTEM FOR CLASSIFYING OPTIC NERVE HEAD

CROSS-REFERENCE TO RELATED APPLICATION

This application claims priority to U.S. patent application Ser. No. 15/821,626, filed on Nov. 22, 2017, which claims priority from Irish Application No. S2016/0260, filed on Nov. 22, 2016, which are incorporated herein by reference.

FIELD OF THE INVENTION

This invention relates generally to image recognition techniques for the eyes of humans or animals, and more specifically to a method and system for detecting characteristics of the optic nerve head of humans or animals and any changes in these characteristics, either due to age, pathology or disease, for the purposes of diagnostics, identification, age assessment, encryption or related analytic applications.

BACKGROUND OF THE INVENTION

The most common forms of preventable and avoidable blindness globally are glaucoma, macular degeneration and diabetic retinopathy. All present with physical changes to the shapes/colours of the normal structures, the nerve and nerve/vascular layer known as the retina, at the back of the eye. Diagnosis of disease is made by direct observation of changes to the normal appearance of these three locations: the circular optic disc, the plain macula and the plain retina and vessel pattern.

Until recently, only highly skilled ophthalmologists and opticians could safely examine the back of the eye using dilating eye drops and complex medical equipment such as ophthalmoscopes and special lenses. In the last decade, major advances in imaging have led to the development of non-mydriatic cameras whereby anyone can take a digital photograph of the back of their eye, simply by placing their head on a chin rest and looking in to the camera. More recently, the ubiquitous mobile phone has camera accessories and fixtures to take the same images. Ongoing research is continuing to image the retinal layers in increasingly fine detail, suggesting the possibility of pre-damage disease detection.

Glaucoma is a condition where the optic nerve is excessively vulnerable and starts to thin out, losing ability to transmit images from the retina to the brain. Early thinning can be detected by observing the changes in the appearance of the optic disc (the head of the nerve where it leaves the eyeball), as illustrated in FIG. 1, as described below. Early detection can mean early treatment and prevention of irreversible sight loss.

In the last decade, new advances in medicine have introduced skilled procedures, such as selective laser trabeculoplasty (SLT) and micro drain implants, which can control previously uncontrolled glaucoma. The preceding decade introduced drugs called prostaglandin inhibitors which transformed the medical management of the majority of previously blinding cases of glaucoma. The fact is that in the developed world, an estimated 50% of patients with glaucoma, "the silent thief", cannot access these new sight saving remedies and glaucoma remain undetected. Once nerve damage has occurred, vision is irretrievably lost.

Photographic examination of the optic nerve head fibres (the optic disc) as they enter the eyeball through the cribriform plate from the brain has only been accessible to specialists until recently. FIG. 1a illustrates a normal optic nerve head and blood vessels within a fundus photograph. FIG. 1b is an image of advanced glaucoma showing large pale 'cup' and thin neuroretinal rim (right). The large paler area (sometimes called the cup) represents the area free of axons where the nerve has been cored out'. The blood vessels branch from the centre (the central retinal artery) which can be seen to be displaced between 12 o clock and 11 o clock on the right of the rim beside the arrow, before it 'bends' up around the rim. In the last decade, major advances in imaging have led to the refinement of non-mydriatic cameras whereby anyone can take a digital photograph of the optic nerve head at the back of their eye simply by placing their head on a chin rest and looking at the camera. More recently, the ubiquitous mobile phone has camera accessories and fixtures using adaptive optics to take equivalent 2D images of the undilated eye. FIG. 2a is a photographic image of an optic disc from a PEEK mobile phone fundus camera attachment. FIG. 2b illustrates an example of a D-Eye phone ophthalmoscope/camera attachment.

Ongoing research is continuing to image the retinal layers in increasingly fine detail, suggesting the possibility of accurate identification, recognition and early nerve fibre disease detection, especially glaucoma. Most advanced clinical imaging of the optic nerve head uses SD-Optical Coherence tomography (OCT), a three-dimensional scanning ophthalmic camera. The latter is too complex for general use although is increasingly applicable for specialized screening.

Almost all studies heretofore have analysed the optic nerve head for glaucoma disease. Furthermore, these studies have focused on what is called the cup-disc ratio, using segmentation of the disc rim minus the inner cup, as a glaucoma index. However, a cup-disc ratio does not definitively indicate axonal optic nerve fibre loss. Furthermore, the ratio is a summary of the measurement of a specific radius of a disc, which is rarely a perfect circle. This is illustrated in FIG. 3, a schematic representation of the optic nerve head photograph images of FIG. 1. Referring to FIG. 3, AB is the center to the rim, and AC is the center to the retina. The cup/disc ratio is the proportion AB to AC. It is also well accepted amongst ophthalmologists that although an increased optic cup-disc ratio suggests a risk of glaucoma, there is a high chance of over fitting with a labeled data set from patients already diagnosed, with an unacceptable chance that glaucoma can progress with loss of axons without affecting the cup/disc ratio.

The use of imaging the retinal blood vessels as a biometric marker has been around for many years, yet it still remains a challenge to develop a safe robust biometric to address shortcomings with current biometrics, such as retinal scans, fingerprints and iris scans. Table 1 summarises relevant research on retinal biometrics. Ahmed et al applied a method using semicircular discs around the optic nerve head with only 84.2 and 89.2% accuracy. Kose et al employ vessel segmentation of similarity (length) measurements with circular sampling.

TABLE 1

Summary of retinal biometric studies

| | | | | |
|---|---|---|---|---|
| Jiu et al. 2016 | Pre-processing with feature extraction Traditional machine learning | Retinal vessel vector analysis of bifurcation points. Vector along length of vessel | Random bifurcation points for circle chosen. Retina analysed | Clinical data sets only, small. 93% accuracy |
| Kose et al 2011 | | Retinal vessel segmentation with circular sampling and vessel length vector | | |
| Drozd 2012 | Retinal vessel bifurcation analysed | Poor optic disc localisation | Retina analysed | 8% best result |
| Bevilacqua et al 2008 | Bifurcation points on retina | Cloud of points | Retina analysed | |
| Ahmed et al 2012 | Optic nerve head | Semicircular segment | Optic nerve head section examined | |

The unique image of the optic nerve head is from a fixed environment without variation in lighting conditions, which hamper pupil size for retinal scans or pupil light change for iris scans. The disc image is inaccessible without full-directed gaze and compliance from the individual, unlike the iris images, which can be captured remotely and reproduced illegally. The optic disc is approximately 1-2 mm in diameter, close to the back of the eye and with unique features making it significantly more accessible, more accurate and easier to image than full retinal blood vessels scans.

It has been suggested that there is a decrease in cup-to-disk ratio and neuroretinal rim area as age increased in studies based on Asian populations. FIG. 4 is a diagrammatic illustration of what happens to the position of the blood vessels in the optic nerve head when thinning of the neuroretinal rim occurs over time. FIG. 5 is a photographic image of the optic nerve head of a patient with progressive glaucoma over ten years, demonstrating enlargement of the central pale area (cup) as the rim thins, with displacement of their blood vessels.

In view of the above, there is a need for an improved method and system for detecting and analysing changes in the optic nerve head.

SUMMARY OF THE INVENTION

The present disclosure provides a computer-implemented method as detailed in claim 1. Advantageous features are provided in dependent claims.

The present disclosure provides a computer-implemented method and system for analysing, categorising and/or classifying characteristics of the optic nerve head, including morphometric and volume characteristics.

The optic nerve is an outpouching of the brain, and its axons (nerve fibres) carry impulses back from the lining of the eye (the retina) to the visual cortex in the brain for vision. The nerve fibres are fed by a central retinal artery and vein, which enter the nerve behind the optic nerve head and branch within the papilla of the optic nerve head to immediately travel over the neuroretinal rim, across Elschnigs line, to the superior and inferior parts of the retina lining the eyeball.

The arrangement of the blood vessels within the optic nerve itself is completely original to every individual eyeball. This arrangement will change as the eyeball grows. In this regard, the relationship of the size and position of the blood vessels and the nerve axons will alter as the nerve and vessels grow at different rates until adulthood. The characteristics of the axon fibres may change if they are lost due to conditions such as glaucoma, or indeed swollen with inflammation or other less common conditions. The characteristics of the blood vessels, like all arteries and veins, may be altered if the pressure of the blood therein increases, causing them to dilate, or harden and constrict, or should diseases such as diabetes or coagulation disorders affect their permeability.

The position of the blood vessels themselves, in relation to their main trunk, and in relation to the axons which they pass through and over in the optic nerve head, will also change when their support/floor of axons changes its position. Loss of axons, such as with glaucoma, will cause a shift in the adjacent vessels and the distance between the centre of the vessel and the other vessel/or neighbouring axons will change. Loss of axons will also change the appearance of the neuroretinal rim.

The present disclosure comprises a computer-implemented method for automatic recognition and identification of the optic nerve head image at the time of image capture. The process uses a deep neural network to segment the optic nerve head from a photographic image of the eye and automatic feature extraction/and or a second deep neural network to train an algorithm to describe the image of the optic disc blood vessels in terms of their proportionality and relationship to each other, based on the angles of the superior and inferior vascular arcade and their branches within the optic nerve head space. The angles of the vessels to the concentric circles change as the positions of the vessels move, causing the length of the vectors from point to point to change as well as training an algorithm to identify the optic nerve axon fibres pattern visible in the 2D optic disc image.

The present disclosure also comprises a process which develops a training algorithm to segment an optic nerve head axon fibres pattern and classify it as glaucomatous or not.

Furthermore, the present disclosure comprises a training algorithm which detects a point where the image of optic nerve head axon fibres and blood vessel proportionality vectors change to indicate either nerve fibre disease and/or blood vessel disease, an example of such specifically being glaucoma progress or acute hypertension or intracranial hypertension.

Furthermore, the present disclosure trains an algorithm to identify the likelihood of the optic nerve head proportionality vectors being that of an adult versus a child, with the probability of determining the age of the optic nerve head and vessels being examined, as will be described later.

The computer-implemented method comprises computer vision algorithms using methods such as filtering, thresholding, edge detection, clustering, circle detection, template matching, transformation, functional analysis, morphology, etc., and machine learning (classification/regression, including neural networks and deep learning) to extract features from the image and classify or analyse them for the purposes described herein. Such analysis shall apply to various methods of imaging the optic nerve head as far as the cribriform plate, including fundus imagery, optical coherence tomography and/or any future medical or commercial imaging technologies, including the use of refractive and colour filters and different wavelengths of light (infrared, near-infrared, ultraviolet, etc.).

The present disclosure will allow for the detection of actual spatial changes due to loss of axons in the neuroretinal rim per se and changes in vessel proportionality independent of cup disc ratio and thus can monitor progressive changes, becoming increasingly sensitive with repeated multiple imaging (as with a self-owned smart phone camera) of the same optic nerve head axons and vessels.

The present disclosure uses a hybrid approach to feature extraction. Deep neural networks are used to segment salient areas of the optic nerve head axons and vessels and further machine learning algorithms are used to extract features to identify and classify the vector relationships of optic nerve head vessels and axons to each other, in order to output:

Identification of optic nerve head ownership
Age of optic nerve head
Health/disease or disease progression status of the optic nerve head The machine learning algorithm can be used to train a deep neural network, or in itself identify and classify an optic nerve head. The methodology of the present disclosure may be used as a biometric, as a detector of glaucoma, as a detector of disease progression and as a determinant of age of the optic disc. The methodology of the present disclosure may be used with all types of fundus cameras, with OCT angiography (OCT-A), with non-mydriatic fundus photography or smartphone fundus imaging for automatic identification and classification of the optic disc and/or with photographs of the optic disc. The methodology of the present disclosure may be used separately or simultaneously on photographic images of right and left optic discs from the same animal/human/species.

BRIEF DESCRIPTIONS OF DRAWINGS

The present disclosure will be more clearly understood by the following description of some embodiments thereof, given by way of example only, with reference to the accompanying drawings, in which:

FIG. 1*a* illustrates a fundus photographic image of a normal optic nerve head and blood vessels and the surrounding retina;

FIG. 1*b* is an image of advanced glaucoma showing large pale 'cup' and thin neuroretinal rim;

FIG. 2*a* is a photographic image of an optic disc from a PEEK mobile phone fundus camera attachment;

FIG. 2*b* illustrates an example of a D-Eye phone ophthalmoscope/camera attachment;

Figure 7A:
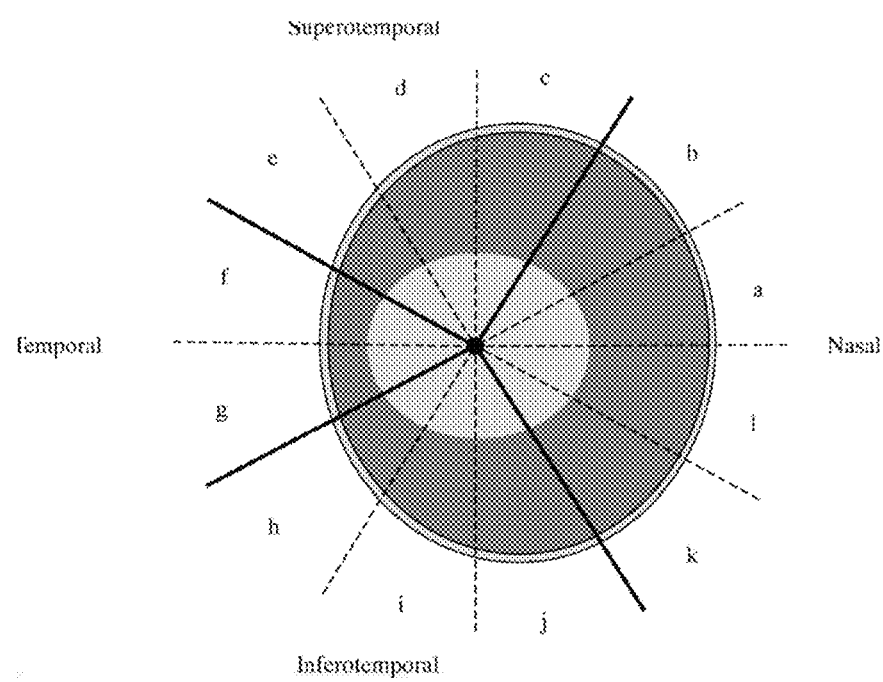
Figure 7B:
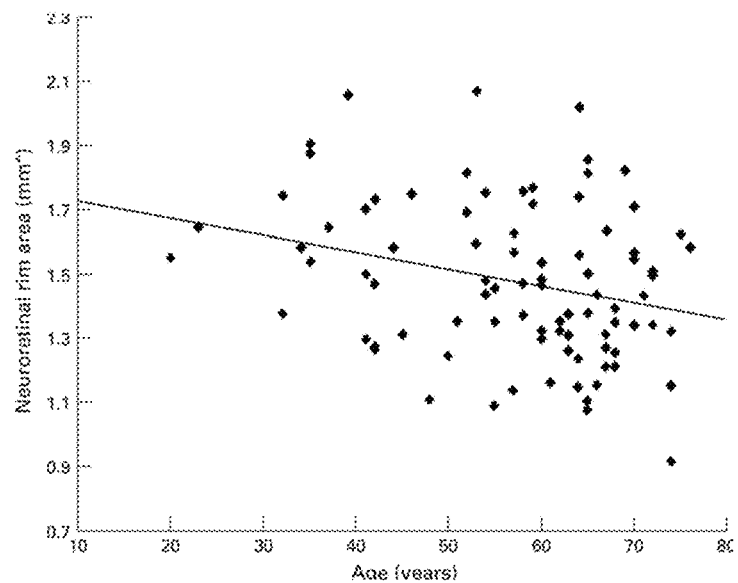
Figure 8A:
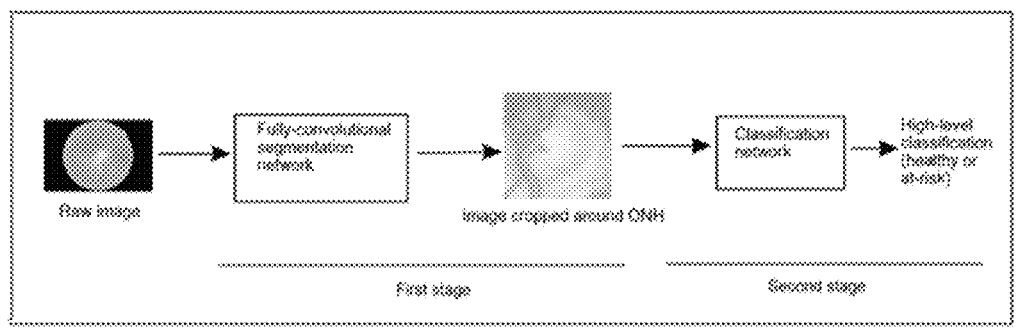
Figure 8B:
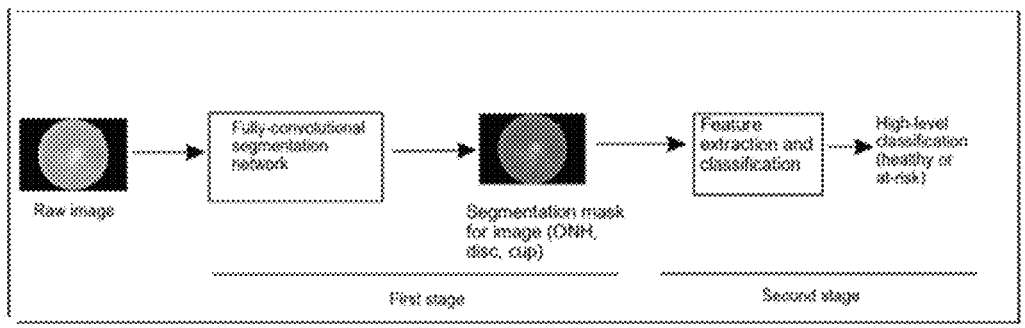
Figure 9:
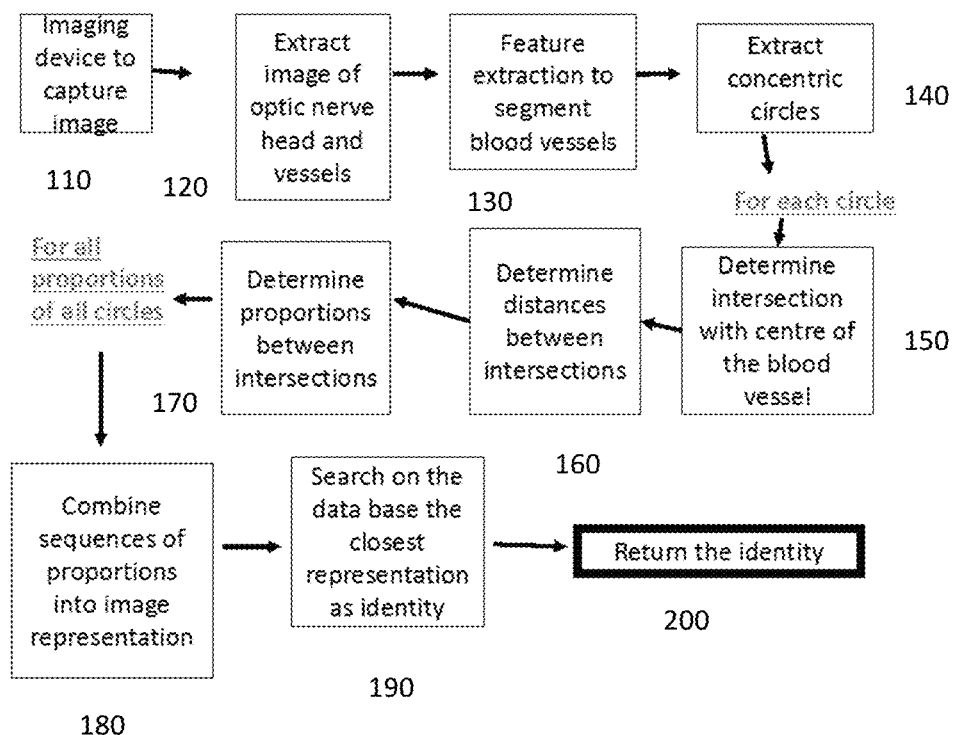
Figure 10A:
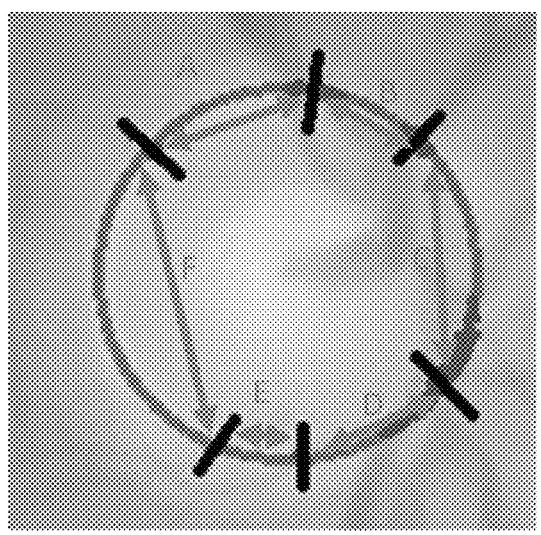
Figure 10B:
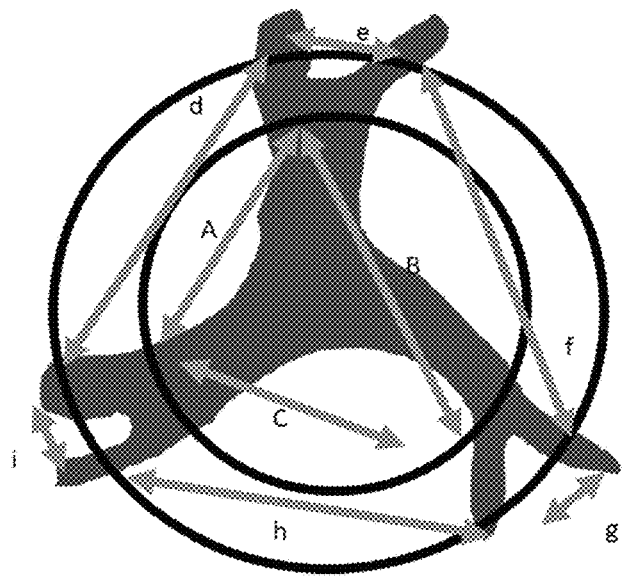
Figure 11:
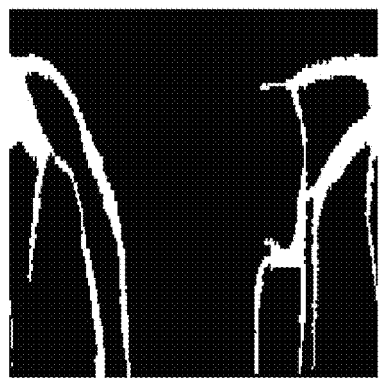
Figure 12:
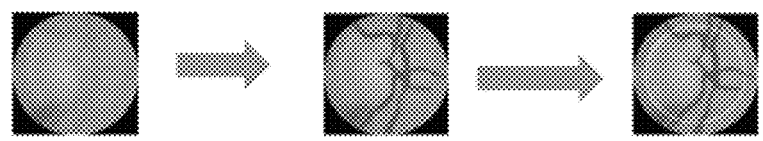
Figures 13, 14:
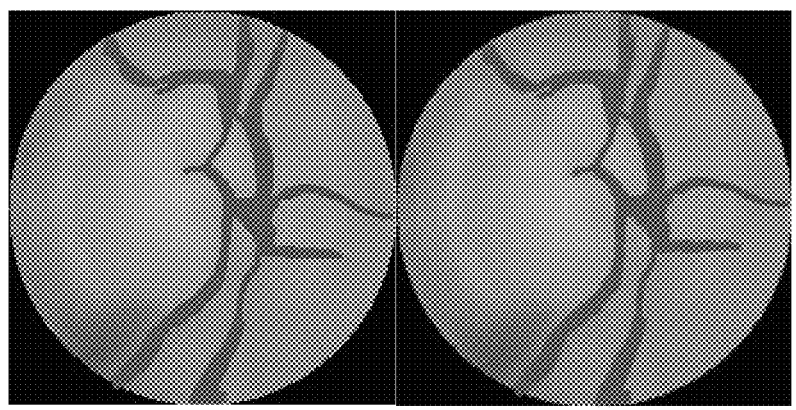
Figure 15A:
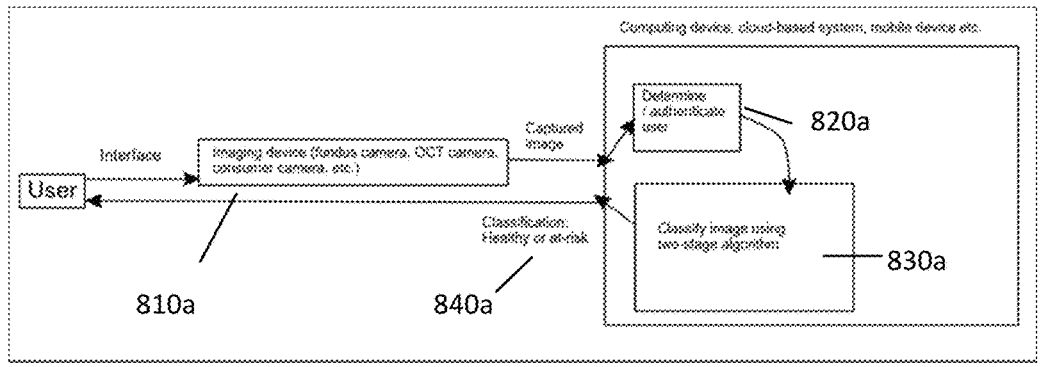
Figure 15B:
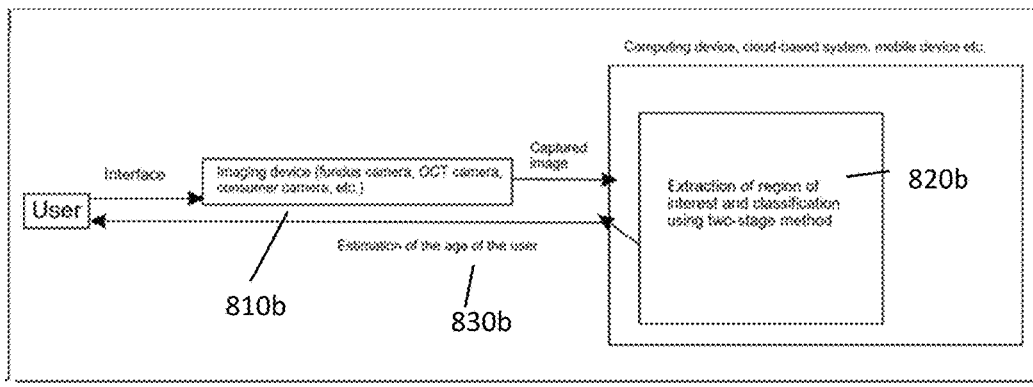
Figure 15C:
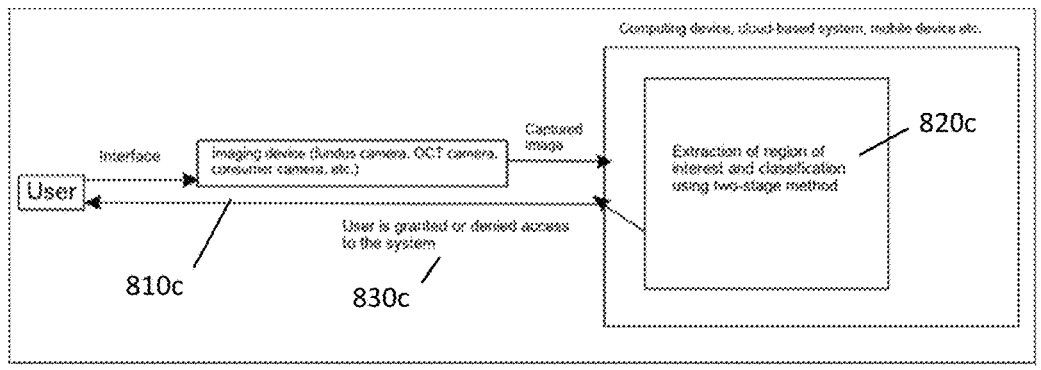
Figure 16:
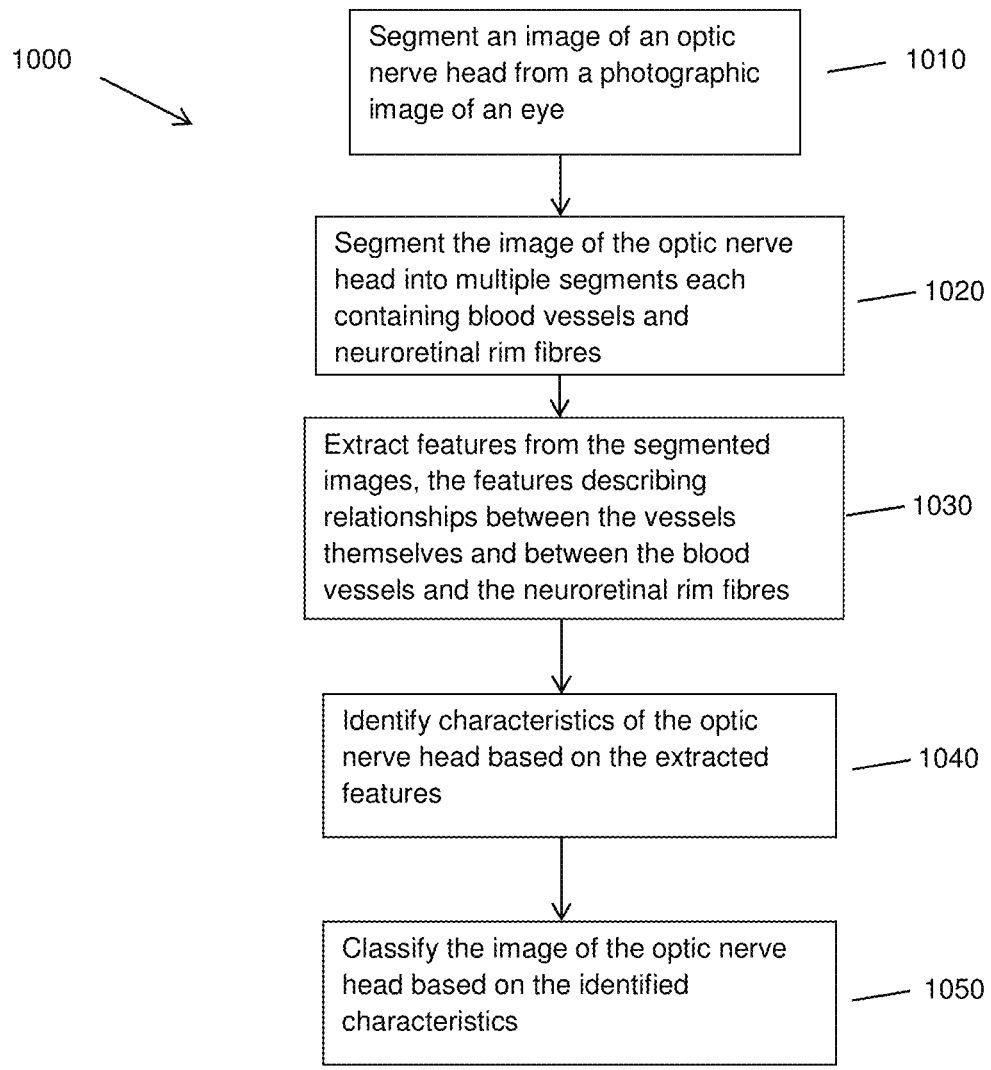
Figure 17:
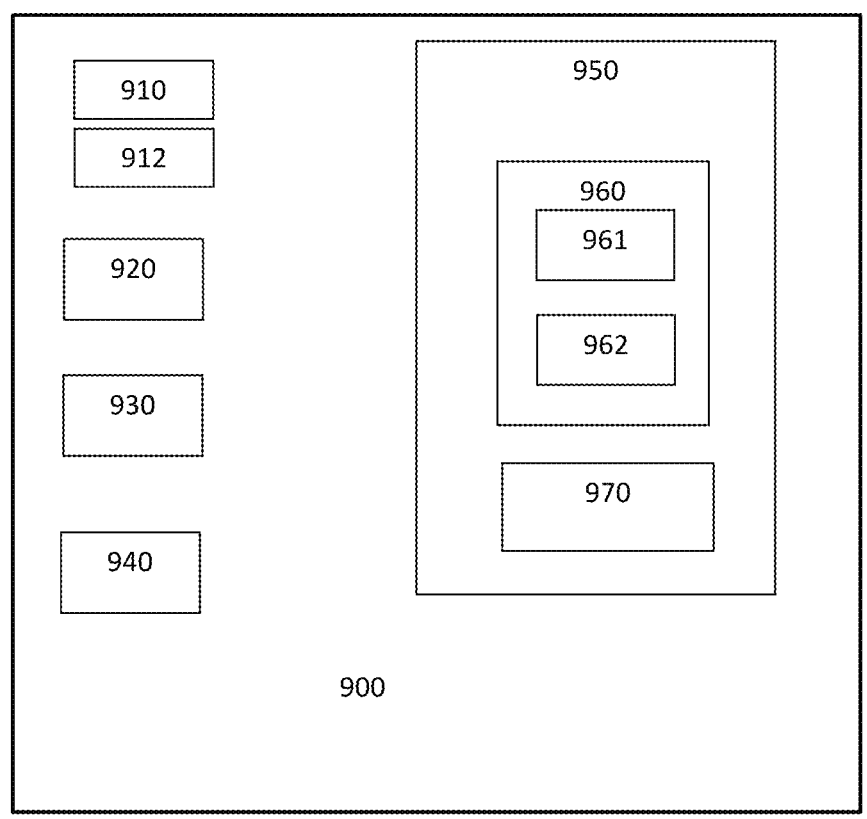

FIG. 7*a* is an image of the optic nerve head divided into segments;

FIG. 7*b* illustrates a graph showing loss of neuroretinal rim according to age;

FIG. 8*a* is a process flow illustrating how an image of the optic nerve head is classified as healthy or at-risk of glaucoma by a dual neural network architecture, according to an embodiment of the present disclosure;

FIG. 8*b* is a process flow illustrating an image of the optic nerve head being cropped with feature extraction prior to classification, according to an embodiment of the present disclosure;

FIG. 9 is a flowchart illustrating an image classification process for biometric identification, according to an embodiment of the present disclosure;

FIG. 10*a* shows one circle of a set of concentric circles intersecting with the optic nerve head vasculature;

FIG. 10*b* is an image of concentric circles in a 200 pixel.sup.2 segmented image intersecting with blood vessels and vector lines;

FIG. 11 is a concatenation of all blood vessel intersections for a given set of concentric circles—this is a feature set;

FIG. 12 illustrates an example of feature extraction with a circle at a radius of 80 pixels, according to an embodiment of the present disclosure;

FIG. 13 illustrates an example of a segmented image of optic nerve head vessels before and after a 4 degree twist with 100% recognition;

FIG. 14 illustrates a table of a sample feature set of resulting cut-off points in pixels at the intersection of the vessels with the concentric circles;

FIGS. 15*a* to 15*c* illustrate a summary of optic nerve head classification processes according to embodiments of the present disclosure;

FIG. 16 is a flowchart illustrating a computer-implemented method of classifying the optic nerve head, according to an embodiment of the present disclosure; and FIG. 17 is a block diagram illustrating a configuration of a computing device which includes various hardware and software components that function to perform the imaging and classification processes according to the present disclosure.

DETAILED DESCRIPTIONS OF THE DRAWINGS

The present disclosure provides a computer implemented method and system for analysing, categorising and/or classifying relationships of characteristics of the optic nerve head axons and its blood vessels therein.

Figure 5:
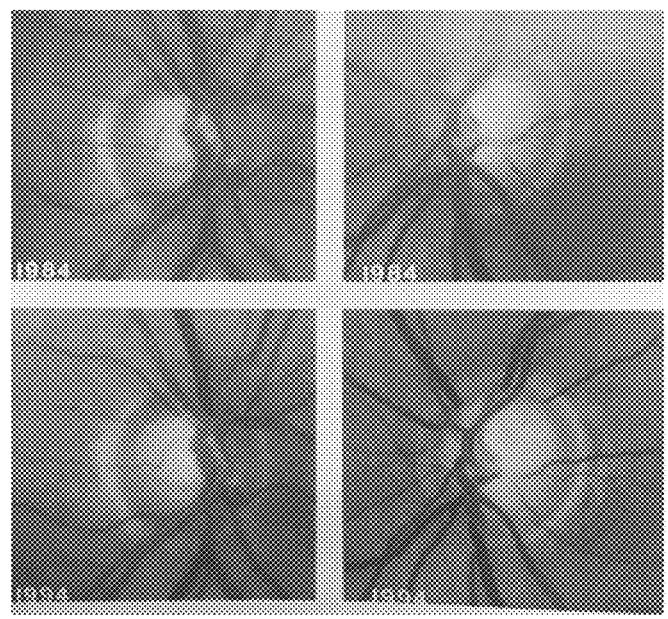
FIG. 5 is a photographic image of the optic nerve head of a patient with progressive glaucoma over ten years, demonstrating enlargement of the central pale area (cup) as the rim thins, with displacement of their blood vessels.
Figure 6:
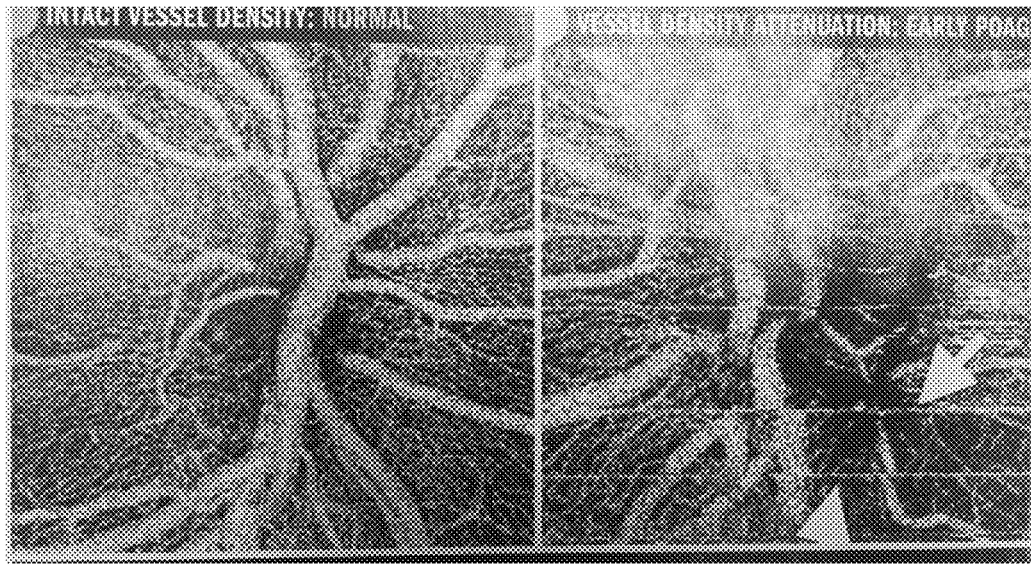
FIG. 6 illustrates OCT angiography (OCT-A) photographic images of a healthy optic nerve head vasculature (on the left) and on the right, a dark gap (between the white arrows) showing loss of vasculature of early glaucoma in a patient with no loss of visual fields.

Machine learning and deep learning are ideally suited for training artificial intelligence to screen large populations for visually detectable diseases. Deep learning has recently achieved success on diagnosis of skin cancer and more relevant, on detection of diabetic retinopathy in large populations using 2D fundus photographs of the retina. Several studies have previously used machine learning to process spectral-domain optical coherence tomography (SD-OCT) images of the retina. Some studies have used machine learning to analyse 2D images of the optic nerve head for glaucoma, including reports of some success with deep learning. Other indicators of glaucoma which have been analysed with machine learning include visual fields, detection of disc haemorrhages and OCT angiography of vasculature of the optic nerve head rim The present disclosure uses convoluted neural networks and machine learning to map the vectors between the vessels and their branches and between the vessels and the neuroretinal rim. These vectors are constant and unique for each optic nerve head and unique for an individual depending on their age. FIGS. 5 and 6 demonstrate results of change in the neuroretinal rim with age by analyzing change in each segment of the rim. As the optic nerve head grows, the position of the blood vessels and their angles to each other changes, and thus their relationship vectors will change as the relationships to the blood vessels and to the axons change. The artificial intelligence is also trained with an algorithm to detect changes in the relationship of the vectors to each other, and to the neuroretinal rim, so that with that loss of axons, such as with glaucoma, change will be detected as a change in the vectors and an indicator of disease progression.

The computer-implemented method may comprise computer vision algorithms, using methods such as filtering, thresholding, edge detection, clustering, circle detection, template matching, transformation, functional analysis, morphology, etc., and machine learning (classification/regression, including neural networks and deep learning) to extract features from the images and classify or analyse the features for the purposes described herein.

The algorithms may be configured to clearly identify the optic disc/nerve head as being most likely to belong to a specific individual to the highest degree of certainty as a means of identification of the specific individual for the purposes of access control, identification, authentication, forensics, cryptography, security or anti-theft. The method may use features or characteristics extracted from optic disc/nerve images for cryptographic purposes, including the generation of encryption keys. This includes the use of a combination of both optic discs/nerves of an individual.

The algorithms may be used to extract features or characteristics from the optic disc/nerve image for the purposes of determining the age of a human or animal with the highest degree of certainty for the purposes of security, forensics, law enforcement, human-computer interaction or identity certification.

The algorithms may be designed to analyse changes in the appearance of the optic nerve disc head/volume attributable to distortion due to inherent refractive errors in the eyeball under analysis. The algorithm may be configured to cross reference inherent changes in size, for example, bigger disc diameter than normal database, smaller disc diameters than normal database, tilted disc head.

The algorithms may include calculation and analyses of ratio of different diameters/volume slices at different multiple testing points to each other within the same optic nerve head, and observing the results in relation to inherent astigmatism and refractive changes within the eyeball of the specific optic nerve. Refractive changes can be due to shape of the eyeball, curvature and power of the intraocular lens and/or curve and power of the cornea of the examined eyeball.

The algorithm may include the detection of a change of artery/vein dimensions as compared with former images of the same optic nerve head vessels and/or reference images of healthy optic nerve head blood vessels.

The algorithm may be used for the purposes of diagnosing changes in artery or vein width to reflect changes in blood pressure in the vessels and/or hardening of the vessels.

The algorithms may be applied to the optic nerve head of humans, of animals including cows, horses, dogs, cats, sheep, goats; including uses in agriculture and zoology.

The algorithms may be used to implement a complete software system used for the diagnosis and/or management of glaucoma or for the storage of and encrypted access to private medical records or related files in medical facilities, or for public, private or personal use.

The algorithms may be configured to correlate with changes in visual evoked potential (VEP) and visual evoked response (VER) as elicited by stimulation of the optic nerve head before, after or during imaging of the optic nerve head.

The algorithms may also model changes in the response of the retinal receptors to elicit a visual field response/pattern of the fibres of the optic nerve head within a 10 degree radius of the macula including the disc head space.

The algorithms may be adapted to analyse the following:
1) Appearance/surface area/pattern/volume of the average optic disc/nerve head/vasculature for different population groups and subsets/racial groups, including each group subset with different size and shaped eyes, including myopic/hypermetropic/astigmatic/tilted disc sub groups, different pigment distributions, different artery/vein and branch distributions, metabolic products/exudates/congenital changes (such as disc drusen/coloboma/diabetic and hypertensive exudates/haemorrhages.
2) Differences in appearance/surface area/pattern/volume of the optic disc/nerve head/vasculature when compared to the average in the population.
3) Differences in appearance/surface area/pattern/volume of the optic disc/nerve head/vasculature when compared to previous images/information from the same patient in the population.
4) Appearance/surface area/pattern/volume of the optic nerve head/vasculature anterior and including the cribriform plate for different population groups and subsets/racial groups, including each group subset with different size and shaped eyes, including myopic/hypermetropic/astigmatic/tilted disc sub groups, including different pigment distributionism, including different artery/vein and branch distributions, including metabolic products/exudates/congenital changes (such as disc drusen/coloboma/diabetic and hypertensive exudates/haemorrhages.
5) Differences in appearance/surface area/pattern/volume of the optic nerve head/vasculature anterior and including the cribriform plate for different population groups and subsets/racial groups, including each group subset with different size and shaped eyes, including myopic/hypermetropic/astigmatic/tilted disc sub groups, including different pigment distributions, including different artery/vein and branch distributions, including metabolic products/exudates/congenital changes (such as disc drusen/coloboma/diabetic and hypertensive exudates/haemorrhages when compared to the average in the population.
6) Differences in appearance/surface area/pattern/volume of the optic nerve head/vasculature anterior and including the cribriform plate for every different population groups and subsets/racial groups, including each group subset with different size and shaped eyes, including myopic/hypermetropic/astigmatic/tilted disc sub groups, including different pigment distributions, including different artery/vein and branch distributions, including metabolic products/exudates/congenital changes (such as disc drusen/coloboma/diabetic and hypertensive exudates/haemorrhages when compared to previous images/information from the same patient in the population.

7) Classifying the remaining optic nerve head and associated vasculature and the ten millimeters deep to the surface, as being normal/abnormal; as being at a high probability of representing a damaged nerve head, as being a volume which is abnormal in relation to the position of other factors at the posterior pole of the fundus, factors/patterns such as distance of the optic nerve head and/or vasculature and rim to the macula; distance to the nasal arcade of arteries and veins, distance to the temporal arcade of veins and arteries.

8) Describing the patterns representing the likelihood of the relationship of the optic nerve outer rim/inner rim/cup/rim pigment/peripapillary atrophy to the fundus vessels/macula as being abnormal; as having changed when compared to an image of the same fundus taken at an earlier time or later time.

9) Attributing the likelihood of the measured volume of optic disc/nerve/vasculature visible to the examiner's eye/camera lens or as measured by OCT/OCT-Angiography as being diagnostic of glaucoma/at risk for glaucoma (all sub groups of glaucoma) and all group of progressive optic nerve disorders/degenerative optic nerve disorders including neuritis/disseminated sclerosis/; as being evidence of being a lower or higher nerve head volume when compared to earlier or later volume or surface area measurements of the same optic nerve head, or being compared to a database/databases of normal, diseased or damaged optic nerve head, in every population subset and racial distribution, particularly Caucasian, Asian, south Pacific and all African races/descendents.

10) Attributing the likelihood of the measured volume/area of optic disc/nerve/vasculature visible to the examiner's eye/camera lens or as measured by OCT/computer vision technology, as being evidence of being a lower or higher nerve head volume when compared to earlier or later volume or surface area measurements of the same optic nerve head, or being compared to a database/databases of normal, diseased or damaged optic nerve head, in every population subset and racial distribution, particularly Caucasian, Asian, south Pacific and all African races/descendents, for all age related changes to the optic nerve/central nervous system, in particular, Alzheimer's disease and diabetic neuropathy and infective nerve disorders such as syphilis/malaria/zika viruses.

11) Clearly identify the optic disc/nerve head and vasculature as being most likely to belong to a specific individual to the highest degree of certainty.

12) Clearly identify the optic disc/nerve head and vasculature as being most likely to belong to a specific individual to the highest degree of certainty as a means of identification of the specific individual for secure access to any location, virtual or special/geographic. For example, a) to replace fingerprint access to electronic/technology innovations, as in mobile phones/computers; to replace password/fingerprint/face photography for secure identification of individuals accessing banking records/financial online data/services.

b) to replace fingerprint access to electronic/technology innovations, as in mobile phones/computers; to replace password/fingerprint/face photography for secure identification of individuals accessing Interpol/international/national security systems c) to replace fingerprint access to electronic/technology innovations, as in mobile phones/computers; to replace password/fingerprint/face photography for secure identification of individuals accessing health records/information data storage/analysis.

The present disclosure provides a computer-implemented method of classifying the optic nerve head, the method comprising operating one or more processors to: segment an image of an optic nerve head from a photographic image of an eye; segment the image of the optic nerve head into multiple segments each containing blood vessels and neuroretinal rim fibres; extract features from the segmented images, the features describing relationships between the blood vessels themselves and between the blood vessels and the neuroretinal rim fibres in each of the segmented images; identify characteristics of the optic nerve head based on the extracted features; and classify the image of the optic nerve head based on the identified characteristics.

It will be understood in the context of the present disclosure that for the purposes of classifying the optic nerve head, the optic nerve head includes the optic nerve head (optic disc) itself and the associated vasculature including blood vessels emanating from the optic nerve head. The optic nerve head also includes neuroretinal rim fibres located in the neuroretinal rim. It will also be understood that image segmentation is the process of dividing or partitioning a digital image into multiple segments each containing sets of pixels. The goal of segmentation is to simplify and/or change the representation of an image into something that is more meaningful and easier to analyse.

The method involves identification of the region of interest, that is the optic nerve head and its vasculature. A deep neural network may be used to segment the image of the optic nerve head and associated blood vessels. The method uses a Deep Neural Network for segmentation of the image. As a non-limiting example, Tensorflow® from Google Python® library was used as follows. Results on a small sample training set had a Sorensen-Dice coefficient of 75-80%.

The method includes automatic high-level feature extraction and classification of the image, for any of the purposes described herein (identification, age determination, diagnosis of optic nerve head vessels and/or axonal fibre loss and/or changes) or a second deep neural network trained to use artificial intelligence to identify/classify the image, for any of the purposes described herein (identification, age determination, diagnosis of optic nerve head vessels and/or axonal fibre loss and/or changes).

Once the image of the optic nerve head and its vasculature is segmented from the image of the eye, the optic nerve head image is further segmented according to the blood vessels within and the optic nerve head neuroretinal rim fibres. Segmentation of the optic nerve head image is illustrated in FIG. 7a. Features are extracted from the segmented images, the features comprising relationships between the vessels themselves and between the blood vessels and the neuroretinal rim. The segmenting the image of the optic nerve head into multiple segments comprises using at least one of machine learning, deep neural networks, and a trained algorithm to automatically identify at least one of i) blood vessel patterns and ii) optic nerve head neuroretinal rim patterns. The relationships between the vessels themselves and between the blood vessels and the neuroretinal rim are described using vectors mapped between points on the blood vessels and the neuroretinal rim in each of the segmented images.

At least one of machine learning, deep neural networks and a trained algorithm may be used to automatically identify the image of at least one of the i) blood vessel patterns and ii) optic nerve head neuroretinal rim patterns as specifically belonging to an individual eye image at that moment in time. The optic nerve head image may be classified as being likely to be glaucomatous or healthy. The optic nerve head image may be classified as being likely to belong to an adult or a child. It may be identified when the said image changes i.e. develops changes to blood vessel relationship and/or optic nerve fibre head, or has changed from an earlier image of the same optic nerve head, such as with disease progression and/or ageing.

The method of the present disclosure can map the vessel relationships and predict the most likely age category of the optic nerve head being examined based on the set of ratios of vessels and vessel to rim and the algorithms form the deep learning data base processing. The neuroretinal rim thickness decreases with age while the position of the vessels will and vector rim distances will drift. FIG. 7b illustrates a graph showing loss of neuroretinal rim according to age. Children's optic nerve heads have a different set of vector values compared to adults.

In more detail, the method may comprise, for each segment: superimposing multiple concentric circles on the segment; determining intersection points of the circles with blood vessels and branches thereof and intersection points between the blood vessels and branches thereof and the neuroretinal rim; mapping vectors between the intersection points; determining distances of the vectors; determining ratios of the vector distances; combining sequences/permutations of the ratios into an image representation; searching a lookup table for the closest representation to the image representation; and classifying the optic nerve head according to the closest representation found.

Several embodiments of the system are detailed as follows. In a first embodiment, as illustrated in FIG. 8a, the image is classified as healthy or at-risk of glaucoma by a dual neural network architecture.

1. A 2D photographic image of an eye may be obtained using a 45 degree fundus camera, a general fundus camera, an assimilated video image, or a simple smartphone camera attachment, or a printed processed or screen image of the optic nerve head, or an image or a photograph of an OCT-A image of an optic nerve head, from either a non-dilated or dilated eye of a human or any other eye bearing species with an optic nerve. A first fully convolutional network may locate the optic nerve head by classifying each pixel in the image of the eye.

2. The fully convolutional network then renders a small geometric shape (e.g. circle) around the optic nerve head and crops the image accordingly.

3. This resulting image can be fed to a trained second convolutional neural network, or have manual feature extraction, which makes a high-level classification of the optic nerve head as healthy or at risk of glaucoma.

In a second embodiment as illustrated in FIG. 8b:
1. A first fully convolutional network identifies a fixed area around the vessel branch patterns.

2. The image is then cropped accordingly and a variety of features are extracted from the resulting image including the vessel to vessel and vessel to nerve fibre ratios.

3. The image is classified as adult or child, and/or including the ability to detect changes with age on the same image in subsequent tests and therefore identify the age of the optic nerve head being segmented using artificial intelligence and/or manual feature extraction.

FIG. 9 is a flowchart illustrating an image classification process for biometric identification, according to an embodiment of the present disclosure. Referring to FIG. 9, the image classification process according to the present embodiment includes using an imaging device to capture an image of the eye 110, segmenting an image of the optic nerve head and its vasculature from the eye image 120, using feature extraction to segment the blood vessels 130, superimposing concentric circles on each of the segmented images 140, for each circle, determining intersection points of the circle with the blood vessels and neuroretinal rim 150, determining distances between the intersection points 160, determining proportions of the distances 170, combining sequences/permutations of the proportions into an image representation 180, and searching a database or lookup table for the closest representation as an identity of the optic nerve head 190 and returning the identify of the optic nerve head 200.

As an experimental non-limiting working example of image classification, the methodology of the present disclosure is further described by reference to the following description and the corresponding results. A data set consisted of 93 optic nerve head images taken at 45 degrees with a fundus camera (Topcon Medical Corporation) with uniform lighting conditions. Images were labelled by ophthalmologists as being healthy or glaucomatous based on neuroretinal rim assessment. Criteria for labelling were based on RetinaScreen. Glaucoma was defined as a disc >0.8 mm in diameter and/or difference in cup-disc ratio of 0.3, followed by ophthalmologist examination and confirmation. The technique was first proofed for 92% concordance with full clinical diagnosis of glaucoma being visual field loss and/or raised intraocular pressure measurements.

The first step, pre-processing, involves a fully convolutional network cropping the image of the eye to a fixed size around the optic nerve head at the outer neuroretinal rim (Elschnig's circle). The blood vessels are manually segmented (see FIG. 7a) into individual blood vessels and branches thereof. Multiple concentric circles are superimposed on each of the segmented images and the intersection of a circle with a specific point on the centre of a blood vessel is extracted, as illustrated in FIG. 10a and FIG. 10b. FIG. 10a shows one circle of a set of concentric circles intersecting with the optic nerve head vasculature. Note the angle between the axes and the vectors reflects changes in direction of the vessel position, as with change in neuroretinal rim volume which causes vessels to shift. FIG. 10b is an image of concentric circles in a 200 pixel.sup.2 segmented image intersecting with blood vessels and vector lines. FIG. 11 is a concatenation of all blood vessel intersections for a given set of concentric circles—this is the feature set. This image is used to match against other feature set images in a database. The Levenstein distance is used to do the similarity match. The image with the lowest Levenstein distance is deemed to be the closest match. A sample feature set is shown in FIG. 12 and the table in FIG. 14. A summary of intersection points is generated from the extracted concentric circles from the center of the optic nerve head in the image of FIG. 12. The white area represents the blood vessels. For each circle 100 points may be extracted, which correspond to an area that belongs to a blood vessel (white), and black relates to intervascular space along the circles. The top border of the picture corresponds to the circle of radius=1 pixel; the lower border corresponds to the circle of radius=100 pixels. FIG. 14 illustrates a table of a sample feature set of resulting cut-off points in pixels at the intersection of the vessels with the concentric circles.

In one example, seven concentric circles may be superimposed on the segmented image from the centre of the optic nerve head with respective ratios of 50, 55, 60, 65, 70, 80 and 90 pixels. The intersection of the circles with the blood vessels is mapped, as illustrated in the flow diagram of FIG. 9, and summarised as shown in FIG. 10. The proportions are calculated using machine learning to classify the extracted sequences and/or permutations of proportions to 1-nearest neighbour (k-NN). k-NN also known as K-Nearest Neighbours is a machine learning algorithm that can be used for clustering, regression and classification. It is based on an area known as similarity learning. This type of learning maps objects into high dimensional feature spaces. The similarity is assessed by determining similarity in these feature spaces (we use the Levenstein distance. The Levenstein distance is typically used to measure the similarity between two strings (e.g. gene sequences comparing AATC to AGTC would have a Levenstein distance of 1). It is called the edit distance because it refers to the number of edits that are required to turn one string into another.

The sequences/permutations of proportions is used as the sequence of original features for the optic disc image.

Example of vector of distances=[A,B,C,D,E,F]

Example of vector of proportions [A/B, B/C, C/D, E/F, F/A].

For each picture, the set of nine vectors of proportions represents its feature set. FIGS. 9 and 11.

Adversarialism was challenged with a 4 degree twist as illustrated in FIG. 13. Adversarialism is the result of a small visually undetectable change in pixels in the image being examined, which in 50% of cases causes convoluted neuronal network algorithms to classify the image as a different one (e.g. a missed diagnosis in a diseased eye). Despite the twist to alter the pixels, the result was still 100% accurate because the change maintained the correct vector relationships which establish the unique identity of the optic nerve fibre head and therefore the reliability of the invention. Leveinstein distance is used to compare the sequences of proportions, where the atomic cost of swapping two proportions is the square value of the difference of the logarithms of the proportions:

Atomic cost=(log(a)−log(b))^2 (the cost of swapping two proportions of different value) Each insertion of deletion has a cost of one unit.

The results are illustrated in FIG. 13. The k-NN algorithm was trained with all 93 pictures. The algorithm was then used to identify an image from the set as being the particular labelled image. 100% of images selected were accurately identified. The images from the training set were then twisted 4 degrees, to introduce images separate to the training set. The algorithm was then challenged to correctly identify the twisted images and accuracy per labelled image was 100%. Taking the correct and incorrect classification as a binomial distribution and using the Clopper-Pearson exact method, it was calculated that with 95% confidence the accuracy of the system is between 96% and 100%.

The Clopper-Pearsons exact method uses the following formula:

$$\left(1+\frac{n-x+1}{xF(1-\alpha/2; 2x, 2(n-x+1))}\right)^{-1} < p < \left(1+\frac{n-x}{(x+1)F(\alpha/2; 2(x+1), 2(n-x))}\right)^{-1}$$

where x is the number of successes, n is the number of trials, and F(c; d1, d2) is the 1-c quantile from an F-distribution with d1 and d2 degrees of freedom.

Note, the first part of the equation is the lower range for the interval and the second then highest, which in this case is 100%.

Figures 1A, 1B:
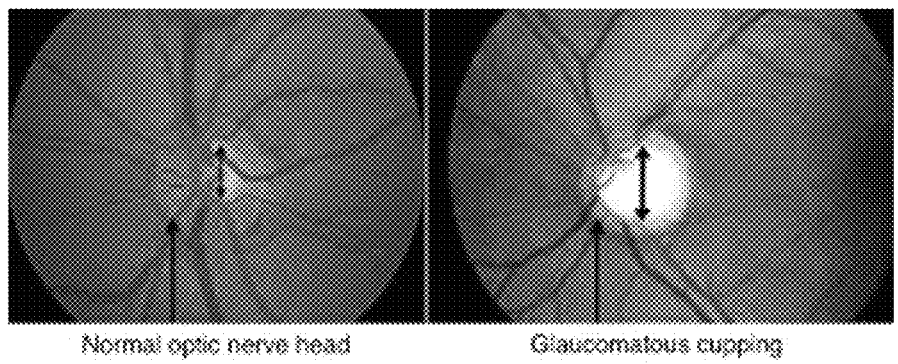
Figure 2A:
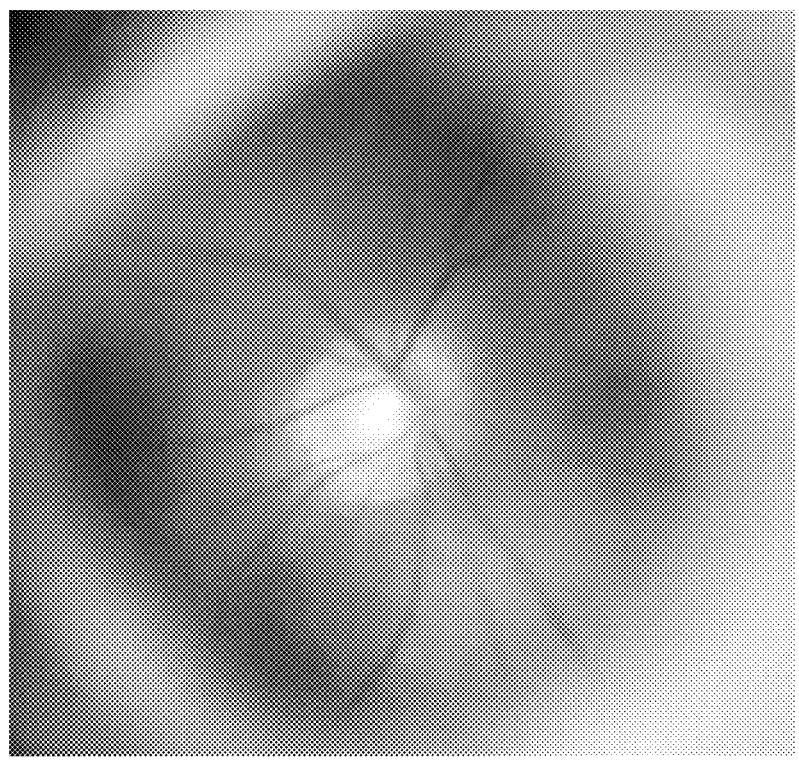
Figure 2B:
Figure 3:
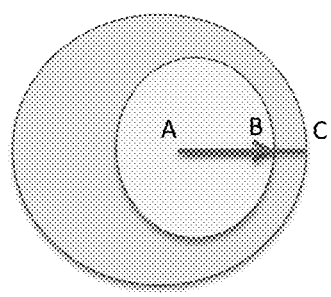
FIG. 3 is a graphic example of the cup/disc ratio (CDR)
Figure 4:
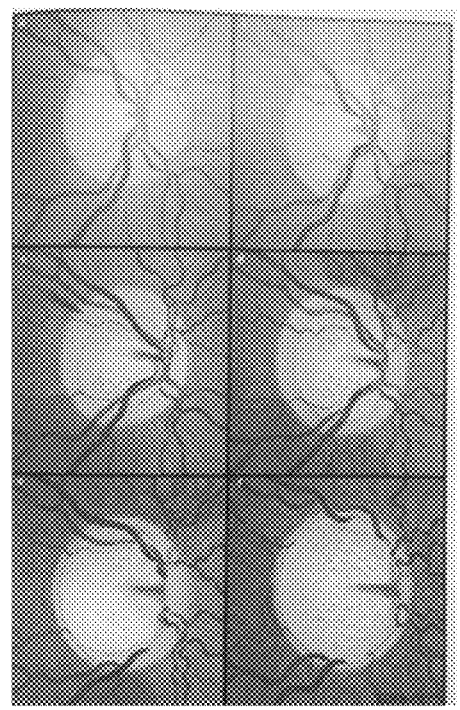
FIG. 4 is a diagrammatic illustration of what happens to the position of the blood vessels in the optic nerve head when thinning of the neuroretinal rim occurs over time.

Table 2 below summarises research with traditional machine learning and deep learning in the region of the optic nerve head and the surrounding retina, emphasizing their differences with the methodology of the present disclosure. None of the research identified the relationships within the optic nerve head of the vessels and axons to each other, nor has any used the relationships for biometric identification or optic disc age assessment. Some studies are performed with three dimensional frequency domain optical coherence tomography (FD-OCT) imaging, which only has achieved 62% sensitivity in screening tests for glaucoma and 92% in clinical sets. Others, such as the present disclosure, use 2D fundus photographs of the retina and optic nerve head. The present disclosure provides the ability to uniquely identify the optic nerve head and its vasculature in order to be able to screen for changes to the optic nerve head and blood vessels with a minimum of 95% specificity and a sensitivity greater than 85% to avoid missing a blinding preventable condition such as glaucoma. Almost all work with traditional machine learning and recent deep learning makes a diagnosis of glaucoma based on a small clinical set commenting only on the vertical cup disc ratio and in a few, textural analysis. Data sets have excluded the general population with all the ensuing morphological and refractive variations, precluding any sensitivity for screening the general population. As mentioned, none has the power to 100% identify the optic nerve head, as with the present disclosure. Identification means the power to state 'not the same' as previous disc identification, i.e., to say the optic nerve head has changed. Almost all studies prior to the present disclosure have analysed the optic nerve head for glaucoma disease and not basic optic nerve head vessels to neuroretinal rim relationship. Furthermore, they have focused on what is called the cup-disc ratio, as illustrated in FIG. 3, using segmentation of the disc outer rim minus the inner cup, as a glaucoma index. However, a cup-disc ratio is not definitively due to axonal optic nerve fibre loss and furthermore, the ratio is a summary of the measurement of a specific radius of a disc which is rarely a perfect circle. It is also well accepted amongst ophthalmologists that although an increased optic cup-disc ratio suggests a risk of glaucoma, there is a high chance of over fitting with a labelled data set from patients already diagnosed, with an unacceptable chance that glaucoma can progress with loss of axons without affecting the cup/disc ratio.

TABLE 2

| | | Summary of machine learning to detect glaucoma | | |
|---|---|---|---|---|
| Jiang liu, 2014 | US Patent U.S. Pat. No. 8,705,826 B2 | Glaucoma diagnosis ARGALI. Cup Disc Ratio detection (CDR) | Automatic Machine learning | Small data set No relationship to vessels or unique identification. |
| Huang et al, 2010 | US Patent Pub. 20100277691 A1 | Glaucoma diagnosis 3 parts of eye: CDR, macula, peripapillae | Automatic Machine learning | No relationship/vessel pattern. FD-OCT. CDR |
| Zhou Zhang 2009 | US Patent Pub. 201020157820A1 | Glaucoma Disc detection with Vessel 'kink' for inner rim | Traditional Machine learning | Disc Haemorrhage only. No vessel relationship/pattern/optic nerve head analysis |
| Chen X et al, 2015 | | Glaucoma Outer disc margin only segmented | Deep learning | No vessel relationship/pattern |
| Claro et al, 2016 | | Optic disc segmentation and Textural feature extraction | Automatic machine learning | 93% accuracy. Small data set, no comment on position of vasculature/relationship to rim. |
| Juan Xu, 2010 | US Patent U.S. Pat. No. 7,992,999B2 | Glaucoma SD-OCT | Automatic learning | Disc margin only, no comment on vasculature. SD-OCT |
| Salam A et al | | Feature extraction and CDR combination | Hybrid structural changes and machine learning | Small data set, restricted to glaucoma diagnosis only; No comment on optic disc vasculature |
| Haleem et al, 2016 | | RIFM Fundus photograph Scanning Laser ophthalmoscopy (SLO) CDR glaucoma data set | Unsupervised machine learning | Double disc diameter (retina and optic nerve head Vessel segmented plus pixel textural analysis) 94% accuracy, CDR used |
| Sedai S et al. 2016 | | Glaucoma CDR | Deep learning | Small data set (50) CDR, clinical dx |
| Fuente-arriega et al 2014 | | Glaucoma Vascular 'bundles' | Machine learning | 93% sensitivity Only three segment analysis of vascular 'bundle' movement |
| Muhammadd H et al 2017 | Hybrid deep learning (HDLM) on OCT | Glaucoma diagnosis. OCT | Hybrid using CNN on OCT results | 87.3% best accuracy for OCT HDLM 93% on retinal nerve fibre. No reference to optic nerve head/vessels. |
| Annan et al 2016 | Deep learning for glaucoma | Combination of CDR and local features | Deep learning using CNN | effective |
| Kanti Roy et al 2017 | Right vs left eye | | Deep learning | Small data set, no analysis of disc |
| Long et al | | Segmented vessels branch pattern analysed | Machine learning | No classification made. |
| Gulshan et al 2017 | Diabetic Retinopathy | | Deep learning | No comment on optic nerve head/vasculature |
| Niemeijer et al | US Patent Pub. 2012213423 | Blood vessel segmentation | | OCT |
| Solanki et al | US Patent U.S. Pat. No. 9,008,391 | Retinal features | Machine learning | Not optic nerve head. Not optic nerve head vasculature relationship and ratios to rim |
| | present disclosure | Identification Age determination Glaucoma progression | Deep and machine learning | 100% Identification specific vessel pattern and relationships within the optic nerve head |

There are a number of possible applications of the methods described herein as follows. One application is to clearly identify the optic nerve head and its vasculature as being most likely to belong to a specific individual to the highest degree of certainty. Here, the second stage of the method is a convolutional neural network trained on a large dataset of fundus images (cropped by a fully convolutional network at the first stage to a fixed geometric shape around the optic nerve head or, in an alternative configuration, cropped to a fixed area around the optic nerve head vessel branch patterns) labeled with identities (with multiple images for each identity) to produce a feature vector describing high-level features on which optic nerve heads can be compared for similarity in order to determine identity. The method may use features or characteristics extracted from optic nerve head images for cryptographic purposes, including the generation of encryption keys. This includes the use of a combination of both optic discs/nerves/vessels of an individual, or as a means of identification of the specific individual for the purposes of use as a biometric, use online to allow access to secure online databases, use with any device to access the device, use with any device to access another device (for example a car). This may be done as a means of identification of the specific individual for secure access to any location, either in cyberspace or through a local hardware device receiving the image of the individual's optic nerve head directly. For example, to replace or be used in combination with other biometric devices, such as fingerprint/retina scan/iris scan in order to access electronic devices such as mobile phones or computers.

Another application can be to determine the age of a human or animal with the highest degree of certainty for the purposes of security, forensics, law enforcement, human-computer interaction or identity certification. Here, the second stage of the method is a convolutional neural network trained on a large dataset of fundus images (cropped by a fully convolutional network at the first stage to a fixed geometric shape around the optic nerve head or, in an alternative configuration, cropped to a fixed area around the optic nerve head vessel branch patterns) labelled for age which can take a new fundus image and classify the age of the individual.

In addition to humans, the algorithms may be applied to the optic nerve head of animals/species including cows, horses, dogs, cats, sheep, goats; including uses in agriculture and zoology. The algorithms may be used to implement a complete software system used for the diagnosis and/or management of glaucoma or for the storage of and encrypted access to private medical records or related files in medical facilities, or for public, private or personal use.

The methodology of the present disclosure may be used to detect changes as the neuroretinal rim area reduces with age. This will have an important role in cybersecurity and the prevention of cyber-crimes relating to impersonation and/or inappropriate access to the internet to/by children.

FIGS. 15a to 15c illustrate a summary of optic nerve head classification processes according to embodiments of the present disclosure. Referring to FIG. 15a, a first process includes capturing an image of the optic nerve head using an imaging device 810a, determining or authenticating the user 820a, classifying the optic nerve head using a two-stage algorithm as described above 830a, and classifying the optic nerve head as healthy or at-risk 840a. Referring to FIG. 15b, a second process includes capturing an image of the optic nerve head of a user using an imaging device 810b, extracting a region of interest using a two-stage algorithm as described above 820b and, and estimating the age of the user 830b. Referring to FIG. 15c, a third process includes capturing an image of the optic nerve head of a user using an imaging device 810c, extracting a region of interest using a two-stage algorithm as described above 820c and, and granting or denying the user access to a system 830c.

FIG. 16 is a flowchart illustrating a computer-implemented method 1000 of classifying the optic nerve head, according to an embodiment of the present disclosure. Referring to FIG. 16, the method comprises operating one or more processors to: segment an image of an optic nerve head from a photographic image of an eye 1010; segment the image of the optic nerve head into multiple segments each containing blood vessels and neuroretinal rim fibres 1020; extract features from the segmented images, the features describing relationships between the blood vessels themselves and between the blood vessels and the neuroretinal rim fibres in each of the segmented images 1030; identify characteristics of the optic nerve head based on the extracted features 1040; and classify the image of the optic nerve head based on the identified characteristics 1050.

FIG. 17 is a block diagram illustrating a configuration of a computing device 900 which includes various hardware and software components that function to perform the imaging and classification processes according to the present disclosure. Referring to FIG. 16, the computing device 900 comprises a user interface 910, a processor 920 in communication with a memory 950, and a communication interface 930. The processor 920 functions to execute software instructions that can be loaded and stored in the memory 950. The processor 920 may include a number of processors, a multi-processor core, or some other type of processor, depending on the particular implementation. The memory 950 may be accessible by the processor 920, thereby enabling the processor 920 to receive and execute instructions stored on the memory 950. The memory 950 may be, for example, a random access memory (RAM) or any other suitable volatile or non-volatile computer readable storage medium. In addition, the memory 950 may be fixed or removable and may contain one or more components or devices such as a hard drive, a flash memory, a rewritable optical disk, a rewritable magnetic tape, or some combination of the above.

One or more software modules 960 may be encoded in the memory 950. The software modules 960 may comprise one or more software programs or applications having computer program code or a set of instructions configured to be executed by the processor 920. Such computer program code or instructions for carrying out operations for aspects of the systems and methods disclosed herein may be written in any combination of one or more programming languages.

The software modules 960 may include at least a first application 961 and a second application 962 configured to be executed by the processor 920. During execution of the software modules 960, the processor 920 configures the computing device 900 to perform various operations relating to the embodiments of the present disclosure, as has been described above.

Other information and/or data relevant to the operation of the present systems and methods, such as a database 970, may also be stored on the memory 950. The database 970 may contain and/or maintain various data items and elements that are utilized throughout the various operations of the system described above. It should be noted that although the database 970 is depicted as being configured locally to the computing device 900, in certain implementations the database 970 and/or various other data elements stored therein may be located remotely. Such elements may be located on a remote device or server—not shown, and connected to the computing device 900 through a network in a manner known to those skilled in the art, in order to be loaded into a processor and executed.

Further, the program code of the software modules 960 and one or more computer readable storage devices (such as the memory 950) form a computer program product that may be manufactured and/or distributed in accordance with the present disclosure, as is known to those of skill in the art.

The communication interface 940 is also operatively connected to the processor 920 and may be any interface that enables communication between the computing device 900 and other devices, machines and/or elements. The communication interface 940 is configured for transmitting and/or receiving data. For example, the communication interface 940 may include but is not limited to a Bluetooth, or cellular transceiver, a satellite communication transmitter/receiver, an optical port and/or any other such, interfaces for wirelessly connecting the computing device 900 to the other devices.

The user interface 910 is also operatively connected to the processor 920. The user interface may comprise one or more input device(s) such as switch(es), button(s), key(s), and a touchscreen.

The user interface 910 functions to facilitate the capture of commands from the user such as an on-off commands or settings related to operation of the system described above. The user interface 910 may function to issue remote instantaneous instructions on images received via a non-local image capture mechanism.

A display 912 may also be operatively connected to the processor 920. The display 912 may include a screen or any other such presentation device that enables the user to view various options, parameters, and results. The display 912 may be a digital display such as an LED display. The user interface 910 and the display 912 may be integrated into a touch screen display.

The operation of the computing device 900 and the various elements and components described above will be understood by those skilled in the art with reference to the method and system according to the present disclosure.

The words comprises/comprising when used in this specification are to specify the presence of stated features, integers, steps or components but does not preclude the presence or addition of one or more other features, integers, steps, components or groups thereof.

The invention claimed is:

1. A computer-implemented method of classifying the optic nerve head, the method comprising operating one or more processors to:
   segment an image of an optic nerve head from a photographic image of an eye;
   segment the image of the optic nerve head into multiple segments each containing blood vessels and neuroretinal rim fibres;
   extract features from the segmented images, the features describing relationships between the blood vessels themselves and between the blood vessels and the neuroretinal rim fibres in each of the segmented images, wherein the relationships between the vessels themselves and between the blood vessels and the neuroretinal rim comprise vectors mapped between points on the blood vessels and the neuroretinal rim in each of the segmented images;
   identify characteristics of the optic nerve head based on the extracted features; and
   classify the image of the optic nerve head based on the identified characteristics.

2. The method of claim 1, comprising segmenting an image of a non-dilated or dilated eye of a human or any other eye bearing species with an optic nerve to obtain an optic nerve head image.

3. The method of claim 1, wherein the segmenting of the image of an optic nerve head from a photographic image of an eye is performed with a deep neural network architecture using a fully convolutional network.

4. The method of claim 3, wherein the optic nerve head is located by classifying each pixel in the image.

5. The method of claim 1, wherein the segmenting of an image of an optic nerve head from a photographic image of an eye comprises rendering a geometric shape around the optic nerve head and cropping the image accordingly.

6. The method of claim 1, wherein the segmenting the image of the optic nerve head into multiple segments comprises using at least one of machine learning, deep neural networks, and a trained algorithm to automatically identify the blood vessels and neuroretinal rim fibers.

7. The method of claim 1, wherein the identifying characteristics of the optic nerve head comprises generating training sets for identifying the relationships between the vessels themselves and between the blood vessels and the neuroretinal rim.

8. The method of claim 1, comprising, for each segment:
   superimposing multiple concentric circles on the segment;
   determining intersection points of the circles with blood vessels and branches thereof and intersection points between the blood vessels and branches thereof and the neuroretinal rim fibres;
   mapping vectors between the intersection points;
   determining distances of the vectors;
   determining ratios of the vector distances;
   combining sequences and/or permutations of the ratios into an image representation;
   searching a lookup table for the closest representation to the image representation; and
   classifying the optic nerve head according to the closest representation found.

9. The method of claim 8, comprising returning an identity of the optic nerve head according to the closest representation found.

10. The method of claim 1, comprising using at least one of machine learning, deep neural networks, and a trained algorithm to automatically identify the blood vessels and optic nerve head neuroretinal rim as belonging to the individual eye image at that moment in time.

11. The method of claim 1, comprising classifying the optic nerve head image as being likely to be glaucomatous or healthy.

12. The method of claim 1, comprising classifying the optic nerve head image as being likely to belong to an adult or a child.

13. The method of claim 1, comprising identifying when the optic nerve head image changes.

14. The method of claim 13, comprising identifying changes to relationships within the optic nerve head image.

15. A computing system configured for classifying the optic nerve head, the computing system comprising:
   a memory; and
   one or more processors configured to:
   segment an image of an optic nerve head from a photographic image of an eye;
   segment the image of the optic nerve head into multiple segments each containing blood vessels and neuroretinal rim fibers;

extract features from the segmented images, the features describing relationships between the blood vessels themselves and between the blood vessels and the neuroretinal rim fibers in each of the segmented images, wherein the relationships between the vessels themselves and between the blood vessels and the neuroretinal rim comprise vectors mapped between points on the blood vessels and the neuroretinal rim in each of the segmented images;

identify characteristics of the optic nerve head based on the extracted features; and classify the image of the optic nerve head based on the identified characteristics.

\* \* \* \* \*